United States Patent
Zeng et al.

(10) Patent No.: US 10,098,820 B2
(45) Date of Patent: Oct. 16, 2018

(54) HIGH SALT TOOTHPASTE WITH STABLE VISCOSITY

(71) Applicant: Colgate-Palmolive Company, New York, NY (US)

(72) Inventors: Yuyan Zeng, Guangzhou (CN); Chengkang Tan, Guangzhou (CN); Pingdong Li, Guangzhou (CN); Yun Xu, Guangzhou (CN)

(73) Assignee: Colgate-Palmolive Company, New York, NY (US)

( * ) Notice: Subject to any disclaimer, the term of this patent is extended or adjusted under 35 U.S.C. 154(b) by 0 days.

(21) Appl. No.: 15/102,534

(22) PCT Filed: Dec. 11, 2013

(86) PCT No.: PCT/CN2013/089047
§ 371 (c)(1),
(2) Date: Jun. 8, 2016

(87) PCT Pub. No.: WO2015/085502
PCT Pub. Date: Jun. 18, 2015

(65) Prior Publication Data
US 2017/0119634 A1    May 4, 2017

(51) Int. Cl.
| | |
|---|---|
| A61K 8/20 | (2006.01) |
| A61Q 11/00 | (2006.01) |
| A61K 8/73 | (2006.01) |
| A61K 8/86 | (2006.01) |
| A61K 8/49 | (2006.01) |
| A61K 8/21 | (2006.01) |
| A61K 8/25 | (2006.01) |
| A61K 8/46 | (2006.01) |
| A61K 8/29 | (2006.01) |
| A61K 8/02 | (2006.01) |
| A61K 6/00 | (2006.01) |

(52) U.S. Cl.
CPC .............. *A61K 8/20* (2013.01); *A61K 6/0047* (2013.01); *A61K 8/0237* (2013.01); *A61K 8/21* (2013.01); *A61K 8/25* (2013.01); *A61K 8/29* (2013.01); *A61K 8/463* (2013.01); *A61K 8/492* (2013.01); *A61K 8/73* (2013.01); *A61K 8/86* (2013.01); *A61Q 11/00* (2013.01); *A61K 2800/48* (2013.01)

(58) Field of Classification Search
CPC .................................................. A61K 6/0047
See application file for complete search history.

(56) References Cited

FOREIGN PATENT DOCUMENTS

| | | |
|---|---|---|
| CN | 85101363 | 1/1987 |
| CN | 101011327 | 8/2007 |
| CN | 102106802 A | 6/2011 |
| JP | S52-90632 A | 7/1977 |
| JP | H05331031 | 12/1993 |

(Continued)

OTHER PUBLICATIONS

WIPO machine translation of Lion Corp (WO 2009/034919A1), accessed Apr. 3, 2017.*

(Continued)

*Primary Examiner* — Benjamin J Packard (57) ABSTRACT

A toothpaste comprising at least 5% sodium chloride and a carrageenan-based binder, having high antibacterial efficacy, very stable viscosity and excellent striping properties, together with methods and uses therefore.

20 Claims, 1 Drawing Sheet

(56) References Cited

FOREIGN PATENT DOCUMENTS

JP      2013-193967 A    9/2013
WO   WO 2009/034919    3/2009

OTHER PUBLICATIONS

International Search Report and Written Opinion for International Application No. PCT/US2013/089047 dated Sep. 23, 2014.

* cited by examiner

HIGH SALT TOOTHPASTE WITH STABLE VISCOSITY

FIELD

The present invention relates to oral care compositions that contain high levels of salt and a novel carrageenan-based binder, and that have very stable viscosity and excellent striping properties.

BACKGROUND

Gum disease affects a significant number of people worldwide, and is a leading cause of tooth loss. Gum disease usually begins with gingivitis, in which bacteria in dental plaque build up, causing the gums to become inflamed. Dental plaque is a soft deposit which forms on teeth and is comprised of an accumulation of bacteria and bacterial by-products. Plaque adheres tenaciously at the points of irregularity or discontinuity, e.g., on rough calculus surfaces, at the gum line and the like. A wide variety of antibacterial agents have been suggested in the art to retard plaque formation. For example, halogenated hydroxydiphenyl ether compounds such as triclosan are well known to the art for their antibacterial activity and have been used in oral compositions to counter plaque formation by bacterial accumulation in the oral cavity. However, while many people would prefer to use natural products such sodium chloride and other natural salts to provide antibacterial activity, the presence of high levels of salt poses special challenges in formulating a toothpaste that has stable viscosity and good striping characteristics. Thus there is a need for novel toothpaste formulations possessing these characteristics. Thus invention is directed to these, as well, as other, important ends.

SUMMARY

Unless otherwise indicated, the terms "%" or "percent" when used in connection with an ingredient of the toothpaste compositions of the invention is intended to refer to the percent by weight of the indicated ingredient in the toothpaste composition.

In some embodiments, the present invention provides a toothpaste composition having high salt concentration and a binder system that provides a stable viscosity over an extended period of time. In some embodiments, the toothpaste composition contains at least 5% sodium chloride by weight. In some further embodiments, the toothpaste contains from 5% to 15% sodium chloride, for example from 8% to 12% sodium chloride. In some embodiments, the toothpaste contains about 10% sodium chloride.

In some embodiments, the binder system includes from carrageenan in an amount of from 0.5% to 1.5%, for example 0.6%, 0.7%, 0.8% 0.9%, 1%, 1.1%, 1.2%, 1.3% or 1.4% by weight of the toothpaste composition. In some embodiments, the binder system optionally also contains one or more carboxymethylcelluloses, in an amount of from 0.1% to 1% by weight of the toothpaste composition; for example from 0.1% to 0.5%; 0.1% to 0.4%; 0.1% to 0.2%; or about 0.3% by weight of the toothpaste composition. In some embodiments, the carboxymethylcellulose is or comprises CMC 2000s.

In further embodiments, the toothpaste further includes one or more humectants. In some embodiments, the humectant is sorbitol, which is present in an amount of from 55% to 70%; or 60% to 66%; or about 63%.

In some embodiments, the carrageenan-binder toothpaste further includes one or more dispersants. In some embodiments, the dispersant is a polyethylene glycol, for example polyethylene glycol 600. In some embodiments, the polyethylene glycol is present in an amount of from 0.5% to 2%, for example 1%.

In some embodiments, the carrageenan-binder toothpaste further includes a thickener, for example thickener silica, in an amount of from 1% to 6%, or from 2% to 4%, for example 3% to 5%, for example 3%, 4% or 5%.

In some embodiments, the carrageenan-binder toothpaste further includes an abrasive, which is preferably an abrasive thickener, in an amount of from 5% to 10%. In some embodiments, the abrasive thickener is silica, in an amount of 5%, 6%, 7%, 8%, 9% or 10%.

In some embodiments, the toothpaste further includes one or more detergents or surfactants. In some embodiments, the toothpaste further includes sodium lauryl sulfate and a poloxamer, for example and without limitation poloxamer 407. In some embodiments, the sodium lauryl sulfate is present in an amount of from 1% to 3% by weight of the toothpaste composition, for example about 2%, and poloxamer 407 is present in an amount of from 0.5% to 2%, for example about 1%.

In some embodiments the toothpaste further includes a fluoride source, for example and without limitation monofluorophosphate (MFP), sodium fluoride, or stannous fluoride. In some embodiments, the fluoride source is sodium fluoride, which is present in an amount of from 0.15% to 0.5%, or from 0.2% to 0.3%.

In some embodiments, the toothpaste further includes one or more adjuvants selected form sweetening agents, flavoring agents and coloring agents. In some embodiments, the toothpaste contains flavoring in an amount of up to 3% by weight of the toothpaste composition; for example from 0.5% to 3.0; 0.8% to 1.6%; or about 1.2%. In some further embodiments, the toothpaste contains one or more sweetening agents in an amount of up to 0.5% by weight of the toothpaste composition; for example up to 0.3%; or from 0.1% to 0.2%.

In some embodiments, the toothpaste includes from 8% to 12% sodium chloride, or 10% sodium chloride; and from 0.6% to 1.1% carrageenan, or 0.7%, 0.8%, 0.9%, or 1.0% carrageenan and, optionally, carboxymethylcellulose, preferably CMC 2000s, in an amount of from 0.1% to 1%, or from 0.1% to 0.5%, or from 0.1% to 0.4%, or from 0.1% to 0.2%, or about 0.3%.

In some embodiments, the toothpaste includes from 8% to 12% sodium chloride; from 0.6% to 1.1% carrageenan; optionally, from 0.1% to 0.5% CMC 2000s, from 55% to 70% sorbitol; and from 0.5% to 2% polyethylene glycol 600.

In some embodiments, the toothpaste includes from 8% to 12% sodium chloride; from 0.6% to 1.1% carageenan; optionally, from 0.1% to 0.5% CMC 2000s; from 60% to 65% sorbitol; and from 0.5% to 2% polyethylene glycol 600.

In some embodiments, the toothpaste includes from 5% to 10% abrasive thickener silica; from 2% to 6% thickener silica; from 1% to 3% sodium lauryl sulfate; from 05% to 2% poloxamer 407; and from 0.1% to 0.5% sodium fluoride.

In some embodiments, the toothpaste includes from 5% to 15% sodium chloride; a binder system comprising from 0.6% to 1.1% carrageenan, and, optionally, from 0.1% to 0.5% carboxymethylcellulose; humectant in an amount of from 60% to 65%; thickener silica in an amount of from 2% to 6%; abrasive thickener in an amount of from 5% to 10%; and a fluoride source. In some such embodiments, the abrasive thickener is silica; the humectant is sorbitol; and the fluoride source is sodium fluoride. In some such embodiments, the toothpaste further includes one or more surfactants or detergents, preferably selected from sodium lauryl sulfate, poloxamer 407 and one or more dispersants, preferably a polyethylene glycol such as polyethylene glycol 600. In some such embodiments, sodium lauryl sulfate is present in an amount of from 1% to 3%; poloxamer 407 or is present in an amount of from 0.5% to 2%; polyethylene glycol 600 is present in an amount of from 0.5% to 2%; and sodium fluoride is present in an amount of from 0.1% to 0.5%.

In some embodiments, the toothpaste includes 8% to 12% sodium chloride; 0.6% to 1.1% carrageenan; optionally 0.1% to 0.5% CMC 2000s; 60% to 65% sorbitol (70 wt % aqueous solution); 0.5% to 1.5% polyethylene glycol 600; 5% to 10% abrasive thickener silica; 1% to 3% sodium lauryl sulfate; 0.5% to 2% poloxamer, e.g., Pluracare F127NF; 2% to 6% thickener silica; and 0.15% to 0.5% sodium fluoride.

In some further embodiments, the invention provides a toothpaste comprising: sodium chloride in an amount of from 6% to 12%; a binder system comprising from 0.5% to 1.5% carrageenan, and, optionally, from 0.1% to 0.5% carboxymethylcellulose; an abrasive; one or more detergents; one or more dispezeants; and a fluoride source; wherein the toothpaste is striped, translucent, and contains more sodium chloride by weight than abrasive.

In some further embodiments, the invention provides a method for stabilizing a toothpaste having high salt concentration, comprising mixing the salt with a binder system, wherein the binder system comprises from 0.5% to 1.5% carrageenan, and, optionally, from 0.1% to 0.5% carboxymethylcellulose.

In some further embodiments, the invention provides the use of carrageenan to stabilize viscosity in a high-salt toothpaste or in the manufacture of a toothpaste according to the present invention.

DETAILED DESCRIPTION

It has been discovered in accordance with the present invention that high levels of salt, for example sodium chloride, can be formulated with a binder system that includes carrageenan as described herein to provide a toothpaste that has a stable viscosity over an extended period of time, excellent striping properties, translucence, and effective antibacterial properties.

The present invention provides toothpaste compositions that contain at least 5% sodium chloride. In some embodiments, the toothpaste compositions of the invention contain from 5% to 15% sodium chloride, with from 8% to 12% sodium chloride being preferred. In some embodiments, the toothpaste contains about 10% sodium chloride. While not wishing to be bound by any theory, the inclusion of high levels of sodium chloride in accordance with the invention is believed to impart antibacterial properties to the compositions, providing benefits in terms of both minimizing bacterial growth during storage and antibacterial efficacy during use.

The binder system of the toothpaste compositions of the present invention contain primarily, or consist of, carrageenan. Carrageenans are known to be linear sulfated polysaccharides that are extracted from red seaweeds. For example, gelatinous extracts of the *Chondrus crispus* (Irish Moss) seaweed are known to be useful as food additives. There are three main varieties of carageenan, designated kappa, iota and lambda, which differ in their degree of sulfation. While any of the kappa, iota or lambda carrageenans are suitable for use with the present invention, iota-carageenan is preferred. In some embodiments, the binder system includes carrageenan in an amount of from 0.5% to 1.5%, for example 0.6%, 0.7%, 0.8% 0.9%, 1%, 1.1%, 1.2%, 1.3% or 1.4% carageenan by weigh by weight of the toothpaste composition.

In some embodiments, the toothpaste compositions of the invention further include one or more birding and/or thickening agents. Birding agents may include polymers include polyethylene glycols, polysaccharides (e.g., cellulose derivatives, for example carboxymethyl cellulose, or polysaccharide gums, for example xanthan gum or carrageenan gum). Acidic polymers, for example polyacrylate gels, may be provided in the form of their free acids or partially or fully neutralized water soluble alkali metal (e.g., potassium and sodium) or ammonium salts; and include synthetic anionic polymeric polycarboxylates, such as 1:4 to 4:1 copolymers of maleic anhydride or acid with another polymerizable ethylenically unsaturated monomer, preferably methyl vinyl ether/maleic anhydride having a molecular weight (MW.) of about 30,000 to about 1,000,000, most preferably about 300,000 to about 800,000. In some embodiments, the binder system contains carrageenan as described above, and one or more binding agents derived from cellulose, preferably a cellulose ether, for example carboxymethylcellulose (CMC), e.g. having a medium to high degree of polymerization, e.g. 1000 to 3000, for example about 2000, e.g., in sodium salt form, e.g., CMC 2000s, in an amount effective to provide the desired viscosity and stability, e.g., from 0.1% to 0.5%, or from 0.1% to 0.4%, or from 0.1% to 0.2%, or about 0.3% by weight of the toothpaste composition.

The toothpaste compositions of the invention further include humectant, i.e. one or more humectants. Examples of suitable humectants include polyhydric alcohols (polyols) such as propylene glycol, glycerin, sorbitol, xylitol or low molecular weight polyethyleneglycols (PEGs). In various embodiments, humectants can prevent hardening of paste or gel compositions upon exposure to air, and also function as sweeteners. In some embodiments, the humectant system consists primarily or solely of sorbitol, e.g., in an amount of from 55% to 70%; or 60% to 66%; or about 63% by weight of the toothpaste composition. However, the presence of other humectants still providing satisfactory toothpaste properties is also contemplated.

In some embodiments, the toothpaste further includes one or more dispersants. In some embodiments, the dispersant is a alkylene glycol such as polyethylene glycol, for example polyethylene glycol 600. In some embodiments, the polyethylene glycol is present in an amount of from 0.5% to 2%, for example 1%.

In some embodiments, the toothpaste compositions of the invention further include one or more thickeners (i.e., thickening agents), which aid in obtaining the proper viscosity of the composition. Generally, the thickener is present in the composition in an amount of from 1% to 6%. Examples of thickening agents include, without limitation, the binding agents described above, which also modify viscosity, for example carboxyvinyl polymers, cellulosic polymers such as hydroxyethylcellulose, carboxymethylcellulose (carmellose) and salts thereof (e.g., carmellose sodium), natural gums such as karaya, xanthan, gum arabic and tragacanth, colloidal magnesium aluminum silicate, colloidal silica, and mixtures thereof. One preferred thickener is thickener silica, in an amount of from 1% to 6%, or from 2% to 4%, for example 2%, 3% or 4%.

In some preferred embodiments, the toothpaste includes from 8% to 12% sodium chloride, or 10% sodium chloride; and from 0.6% to 1.1% carrageenan, or 0.7%, 0.8%, 0.9%, or 1.0% carrageenan and, optionally, carboxymethylcellulose, preferably CMC 2000s, in an amount of from 0.1% to 1%, or from 0.1% to 0.5%, or from 0.1% to 0.4%, or from 0.1% to 0.2%, or about 0.3%.

The toothpaste compositions further comprise an abrasive, e.g. selected from abrasive silica and/or calcium salts, e.g. calcium carbonate and/or a calcium phosphate abrasive, e.g., tricalcium phosphate ($Ca_3(PO_4)_2$), hydroxyapatite ($Ca_{10}(PO_4)_6(OH)_2$), or dicalcium phosphate dihydrate ($CaHPO_4.2H_2O$, also sometimes referred to herein as DiCal) or calcium pyrophosphate. In a particular embodiment, the abrasive includes or is composed of silica, for example abrasive thickener silica in an amount of from 5% to 10%, or 5%, 6%, 7%, 8%, 9% or 10% by weight of the toothpaste composition.

The toothpaste compositions of the invention can further include one or more detergents or surfactants. Surfactants useful for the present invention include, without limitation: anionic, nonionic, and amphoteric surfactants. Surfactants may be used, for example, to provide enhanced stability of the formulation, to help in cleaning the oral cavity surfaces through detergency, and to increase foaming of the composition upon agitation, e.g., during brushing. Suitable anionic surfactants include, for example, water-soluble salts of $C_{8-20}$ alkyl sulfates, sulfonated monoglycerides of $C_{8-20}$ fatty acids, sarcosinates and taurates; for example sodium lauryl sulfate, sodium coconut monoglyceride sulfonate, sodium lauryl sarcosinate, sodium lauryl isoethionate, sodium laureth carboxylate and sodium dodecyl benzenesulfonate, and mixtures thereof. Suitable nonionic surfactants include, for example, poloxamers, polyoxyethylene sorbitan esters, fatty alcohol ethoxylates, alkylphenol ethoxylates, tertiary amine oxides, tertiary phosphine oxides, dialkyl sulfoxides, and mixtures thereof. In one embodiment, the toothpaste comprises sodium lauryl sulfate, for example in an amount of from 1% to 3%, or about 2%. The toothpaste may also or alternatively contain one or more nonpolar surfactants, for example polymers and co-polymers of ethylene glycol and propylene glycol, e.g., poloxamers, i.e., nonionic triblock copolymers composed of a central hydrophobic chain of polyoxypropylene (poly(propylene oxide)) flanked by two hydrophilic chains of polyoxyethylene (poly(ethylene oxide)). The approximate lengths of the two PEG blocks is, in some embodiments, an average of about 50-150 repeat units, e.g., about 100 repeat units while the approximate length of the propylene glycol block is an average of about 25-75 repeat unties, e.g., about 50-60 repeat units. In one embodiment, the poloxamer is poloxamer 407, also known by the BASF trade name Pluronic F127, e.g., in an amount of from 0.5% to 2%, for example about 1%. For example, in certain embodiments, the toothpaste compositions of the invention may contain both sodium lauryl sulfate and a poloxamer such as poloxamer 407. In some embodiments, the sodium lauryl sulfate is present in an amount of from 1% to 2%, for example about 2%, and the poloxamer such as poloxamer 407 is present in an amount of from 0.5% to 2%, for example about 1%, by weight of the toothpaste composition.

The toothpaste compositions of the present invention may also contain a fluoride source—i.e., a fluoride-containing compound having a beneficial effect on the care and hygiene of the oral cavity, e.g. diminution of enamel solubility in acid and protection of the teeth against decay. Examples of suitable fluoride sources include sodium fluoride, stannous fluoride, potassium fluoride, potassium stannous fluoride (SNFZ-KF), potassium fluorozirconate, sodium hexafluorostannate, stannous chlorofluoride, and sodium monofluorophosphate (MFP). Where present, the fluoride source would provide fluoride ion in amounts sufficient to supply about 25 ppm to about 25,000 ppm of fluoride ions, generally at least about 500 ppm, e.g., about 500 to about 2000 ppm, e.g., about 1000 to about 1600 ppm, e.g., about 1450 ppm. The appropriate level of fluoride will depend on the particular application. A toothpaste for general consumer use would typically have about 1000 to about 1500 ppm, with pediatric toothpaste having somewhat less. A dentifrice or coating for professional application could have as much as about 5,000 or even about 25,000 ppm fluoride. The amount by weight of these materials, which dissociate or release fluoride or fluorine-containing ions, will depend on the molecular weight of the counterion as well as on the particular application, but suitably may be present in an effective but non-toxic amount, usually within the range of 0.1 to 2% by weight. In some embodiments, a fluoride source selected from sodium fluoride, stannous fluoride, sodium monofluorophosphate and mixtures thereof, is used, for example the toothpaste of the invention may comprise an effective amount of sodium monofluorophosphate. In some embodiments, the fluoride source is sodium fluoride, which is present in an amount of from 0.15% to 0.5%, or from 0.2% to 0.3% by weight of the toothpaste composition.

As will be evident to one of skill in the art, some components of the invention may perform multiple functions, and the identification of a compound as having one function herein is not meant to exclude its use for other functions in a particular composition. For example, a compound such as carboxymethylcellulose may act as a binder, but also has humectant and thickening properties, or a compound such as a Poloxamer, while identified above as a nonionic surfactant, also has humectant and thickening properties, and a compound such as polyethylene glycol 600, while identified above as a dispersant, also may function as a diluent and/or humectant.

It is also understood that compounds in formulation may naturally react, disassociate, and/or form complexes with one another. Accordingly, certain ingredients may be formed in situ (for example, it is understood that sodium chloride may be formed by reacting sodium hydroxide with hydrochloric acid), and also may in formulation exist in different forms (for example, to the extent the sodium chloride is dissolved, it will naturally disassociate into separate sodium and chloride ions, as opposed to a solid salt). As is usual in the art, the compositions of the invention are described in terms of exemplary formulation ingredients, without intending to exclude combinations of other ingredients that result in the same final compositions, or to exclude the natural reaction products of the described ingredient combinations.

In some embodiments described above, the toothpaste compositions of the invention can further include one or more sweetening agents, flavoring agents and coloring agents. Any suitable flavoring or sweetening material may be employed. Examples of suitable flavoring constituents include flavoring oils, e.g. oil of spearmint, peppermint, wintergreen, clove, sage, *eucalyptus*, marjoram, cinnamon, lemon, and orange, and methyl salicylate. Suitable sweetening agents include sucrose, lactose, maltose, xylitol, sodium cyclamate, perillartine, AMP (aspartyl phenyl alanine methyl ester), saccharine and the like. Suitably, flavor and sweetening agents may each or together comprise from about 0.1% to 5% more of the oral car composition. In some embodiments, the toothpaste compositions of the invention include one or more flavoring agents in an amount of from about 0.5% to about 3.0%; about 0.8% to about 1.6%; or about 1.2%. In some further embodiments, the toothpaste contains one or more sweetening agents in an amount of up to 0.5% by weight of the toothpaste composition; for example up to 0.3%; or from 0.1% to 0.2%.

Various other materials may be incorporated in the oral preparations of this invention such as whitening agents, including urea peroxide, calcium peroxide, titanium dioxide, hydrogen peroxide, complexes of polyvinylpyrolidone (PVP) and hydrogen peroxide, preservatives, vitamins such as vitamin B6, B12, E and K, silicones, chlorophyll compounds, potassium salts for the treatment of dental hypersensitivity such as potassium nitrate as well as antitartar agents such as sodium tripolyphosphate and di- and tetra-alkali metal pyrophosphate salts such as di- and tetrasodium pyrophosphate. These agents, when present, are incorporated in the compositions of the present invention in amounts which do not substantially adversely affect the properties and characteristics desired.

In general, each of the foregoing adjuvants may be typically incorporated in the instant toothpastes in amounts up to 5% provided they do not adversely affect the stability and cleaning properties of the non-bleeding striped dentifrice of present invention.

In some embodiments, the carageenan-binder toothpaste includes from 5% to 15% sodium chloride; a binder system comprising from 0.6% to 1.1% carrageenan, and, optionally, from 0.1% to 0.5% carboxymethylcellulose; thickener silica in an amount of from 2% to 6%; abrasive thickener in an amount of from 5% to 10%; humectant in an amount of from 60% to 65%; and a fluoride source. In some such embodiments, the abrasive thickener is silica; the humectant is sorbitol; and the fluoride source is sodium fluoride. In some such embodiments, the toothpaste further includes one or more surfactants or detergents, preferably selected from sodium lauryl sulfate, poloxamer 407 and Pluracare F127NF, and one or more dispersants, preferably a polyethylene glycol such as polyethylene glycol 600. In some such embodiments, sodium lauryl sulfate is present in an amount of from 1% to 3%; Poloxamer 407 or Pluracare F127NF is present in an amount of from 0.5% to 2%; polyethylene glycol 600 is present in an amount of from 0.5% to 2%; and sodium fluoride is present in an amount of from 0.1% to 0.5%.

In some embodiments, the toothpaste includes 8% to 12% sodium chloride; 0.6% to 1.1% carrageenan; optionally 0.1% to 0.5% CMC 2000s; 60% to 65% sorbitol (70 wt % aqueous solution); 0.5% to 1.5% polyethylene glycol 600; 5% to 10% abrasive thickener silica; 1% to 3% sodium lauryl sulfate; 0.5% to 2% Pluracare F127NF; 2% to 6% thickener silica; and 0.15% to 0.5% sodium fluoride.

In some further embodiments, the invention provides a toothpaste comprising: sodium chloride in an amount of from 6% to 12%; a binder system comprising from 0.5% to 1.5% carrageenan, and, optionally, from 0.1% to 0.5% carboxymethylcellulose; an abrasive; one or more detergents; one or more dispersants; and a fluoride source; wherein the toothpaste is striped, translucent, and contains more sodium chloride by weight than abrasive.

In some further embodiments, the invention provides a method for stabilizing a toothpaste having high salt concentration, comprising mixing the salt with a binder system, wherein the binder system comprises from 0.5% to 1.5% carrageenan, and, optionally, from 0.1% to 0.5% carboxymethylcellulose.

The invention thus provides, in one embodiment, a toothpaste comprising at least 5% sodium chloride; from 5% to 15% sodium chloride; from 8% to 12% sodium chloride; or about 10% sodium chloride (Composition 1), together with a binder and humectant, for ex ample:

1.1. Composition 1, wherein the binder system comprises a carrageenan, in an amount of from 0.5% to 1.5%, or 0.6%, 0.7%, 0.8%, 0.9%, 1%, 1.1%, 1.2%, 1.3% or 1.4% by weight of the toothpaste composition.

1.2. Any foregoing composition wherein the binder system comprises a cellulose derivative, e.g., carboxymethylcellulose (CMC), e.g. having a medium to high degree of polymerization, e.g. 1000 to 3000, for example about 2000, e.g., in sodium salt form, e.g., CMC 2000s, in an amount effective to provide the desired viscosity and stability, e.g., from 0.1% to 0.5%, or from 0.1% to 0.4%, or from 0.1% to 0.2%, or about 0.3% by weight of the toothpaste composition.

1.3. Any foregoing composition wherein the humectant comprises a polyol, e.g., sorbitol, e.g., sorbitol in an amount of from 55% to 70%; or 60% to 66%; or about 63% by weight of the toothpaste composition.

1.4. Any foregoing composition further comprising one or more dispersants e.g., polyethylene glycol, for example polyethylene glycol 600, in an amount of from 0.5% to 2%, or about 1% by weight of the toothpaste composition.

1.5. Any foregoing composition further comprising one or more thickeners, e.g., thickener silica, in an amount of from 1% to 6%, or from 2% to 4%, or 2%, 3% or 4% by weight of the toothpaste composition.

1.6. Any foregoing composition further comprising one or more abrasives, which is preferably an abrasive thickener, e.g., abrasive thickener silica, in an amount of from 5% to 10%, or 5%, 6%, 7%, 8%, 9% or 10% by weight of the toothpaste composition.

1.7. Any foregoing composition further comprising one or more anionic detergents or surfactants, e.g., sodium lauryl sulfate, in an amount of from 1% to 3%, or about 2%; and one or more nonionic surfactants, e.g., a poloxamer, e.g., poloxamer 407, in an amount of from 0.5% to 2%; or about 1%.

1.8. Any foregoing composition further comprising an effective amount of a fluoride ion source; e.g., sodium fluoride, in an amount of from 0.15% to 0.5%, or from 0.2% to 0.3%.

1.9. Any foregoing composition comprising:
from 8% to 12% sodium chloride;
from 0.6% to 1.1% carrageenan;
optionally, from 0.1% to 0.5% CMC 2000s;
from 55% to 70% sorbitol;
from 0.5% to 2% polyethylene glycol 600;
from 5% to 10% abrasive thickener silica;
from 2% to 6% thickener silica;
from 1% to 3% sodium lauryl sulfate;
from 0.5% to 2% poloxamer 407; and
from 0.1% to 0.5% sodium fluoride.

1.10. The toothpaste of any foregoing composition, comprising from 55% to 70% sorbitol.

1.11. The toothpaste of any foregoing compositions, further comprising one or more adjuvants selected from sweetening agents flavoring agents and coloring agents, e.g., comprising a flavoring agent in an amount of from 0.5% to 3.0%; 0.8% to 1.6%; or about 1.2%.

1.12. Any foregoing composition comprising 10% sodium chloride; 0.9% to 1.5% carrageenan optionally, 0.1% to 0.5% CMC 2000s about 63% sorbitol; about 1% polyethylene glycol; 3% to 4% thickener silica; 5% to 10% abrasive silica thickener; about 2% sodium lauryl sulfate; about 1% poloxamer 407; and 0.2% to 0.3% so dun fluoride.

The invention further provides in another embodiment, a method for reducing bacterial growth in a toothpaste comprising a silica abrasive, comprising including at least 5% sodium chloride; from 7.5% to 12.5% sodium chloride; or about 10% sodium chloride in the toothpaste.

The invention further provides, in another embodiment, a toothpaste comprising sodium chloride in an amount of from 8% to 12%; a binder system comprising from 0.5% to 1.5% carrageenan, and, optionally, from 0.1% to 0.5% carboxymethylcellulose; an abrasive; one or more detergents; one or more dispersants; and a fluoride source; wherein the toothpaste is striped, translucent, and contains more sodium chloride by weight than abrasive.

The invention further provides in another embodiment, a method for reducing bacterial growth in an oral cavity, comprising contacting the oral cavity with a toothpaste of any of Compositions 1, at seq.

The invention further provides, in another embodiment, the use of carrageenan to stabilize viscosity in a high-salt toothpaste or in the manufacture of a toothpaste according to any of Compositions 1, at seq.

The invention further provides, in another embodiment, a method for stabilizing a toothpaste having high salt concentration, comprising mixing the salt with a binder system, wherein the binder system comprises from 0.5% to 1.5% carrageenan, and, optionally, from 0.1% to 0.5% carboxymethylcellulose.

The following examples are further illustrative of the nature of the present invention, but it is understood that the invention is not limited thereto. All amounts and proportions referred to herein and in the appended claims are by weight, unless otherwise indicated.

Example 1—Binder System Determination

Several thickener/binder systems containing high sodium chloride concentrations were evaluated for their ability to maintain viscosity over time. Table 1 shows the compositions of experimental formulas 1-9, and control formula 10. Formulas 1-8 contain 10% sodium chloride and formula 9 contains 5% sodium chloride.

TABLE 1

Compositions of Toothpaste Formulas

| Ingredient | Formula 1 | 2 | 3 | 4 | 5 | 6 | 7 | 8 | 9 | Control |
|---|---|---|---|---|---|---|---|---|---|---|
| Sorbitol (70 wt % aqueous solution) | 63.0 | 63.0 | 63.0 | 63.0 | 63.0 | 63.0 | 63.0 | 63.0 | 63.0 | 40.0 |
| Polyethylene Glycol 600 | 1.0 | 1.0 | 1.0 | 1.0 | 1.0 | 1.0 | 1.0 | 1.0 | 1.0 | / |
| Sodium Saccharin | 0.15 | 0.15 | 0.15 | 0.15 | 0.15 | 0.15 | 0.15 | 0.15 | 0.15 | 0.30 |
| Sodium Fluoride | 0.22 | 0.22 | 0.22 | 0.22 | 0.22 | 0.22 | 0.22 | 0.22 | 0.22 | 0.32 |
| Abrasive Silica | 8.0 | 8.0 | 8.0 | 8.0 | 8.0 | 8.0 | 8.0 | 8.0 | 8.0 | 15.0 |
| Sodium Lauryl Sulfate | 2.0 | 2.0 | 2.0 | 2.0 | 2.0 | 2.0 | 2.0 | 2.0 | 2.0 | 2.0 |
| Flavor | 1.2 | 1.2 | 12 | 12 | 12 | 12 | 1.2 | 12 | 1.2 | 1.15 |
| Sodium Chloride | 10.0 | 10.0 | 10.0 | 10.0 | 10.0 | 10.0 | 10.0 | 10.0 | 5.0 | / |
| Titanium Dioxide | 0.5 | 0.5 | 0.5 | 0.5 | 0.5 | 0.5 | 0.5 | 0.5 | 0.5 | 0.6 |
| Pluracare F127NF | 1.0 | 1.0 | 1.0 | 1.0 | 1.0 | 1.0 | 1.0 | 1.0 | 1.0 | / |
| Water | 6.43 | 7.53 | 5.63 | 4.63 | 4.68 | 8.93 | 9.13 | 9.08 | 12.83 | 29.423775 |
| Thickener Silica | 6.0 | 5.0 | 7.0 | 8.0 | 8.0 | 3.0 | 3.0 | 3.0 | 4.0 | 1.5 |
| Sorbosil AC43 | / | / | / | / | / | / | / | / | / | 5.0 |
| Pigment Yellow | / | / | / | / | / | / | / | / | / | 0.0155 |
| Pigment Red | / | / | / | / | / | / | / | / | / | 0.000723 |
| Sodium Hydrate (50%) | / | / | / | / | / | / | / | / | / | 1.375 |
| Gantrez S-97 Powder | / | / | / | / | / | / | / | / | / | 2.0 |
| Propolis Extract | / | / | / | / | / | / | / | / | / | 0.015 |
| Triclosan | / | / | / | / | / | / | / | / | / | 0.30 |
| Carrage enan | / | / | / | / | / | 1.0 | 0.8 | 0.70 | 0.8 | 1.0 |
| CMC TMS | 0.3 | / | / | / | / | / | / | / | / | / |

TABLE 1-continued

Compositions of Toothpaste Formulas

| Ingredient | Formula | | | | | | | | | Control |
|---|---|---|---|---|---|---|---|---|---|---|
| | 1 | 2 | 3 | 4 | 5 | 6 | 7 | 8 | 9 | |
| CMC 2000S | / | 0.2 | 0.3 | 0.3 | 0.25 | / | / | 0.15 | 0.3 | / |
| Xanthan Gum | 0.2 | 0.2 | / | / | / | / | / | / | / | / |
| Total | 100 | 100 | 100 | 100 | 100 | 100 | 100 | 100 | 100 | 100 |

The viscosity data obtained for the thickener/binder systems are shown below in Table 2.

TABLE 2

Viscosity data for different thickener/binder systems (×10$^4$ cps)

| Formula\Time | 0 hr | 1 hr | 2 hrs | 3 hrs | 24 hrs | 1 month | 2 months | 3 months |
|---|---|---|---|---|---|---|---|---|
| 1 | 21.4 (38.8° C.) | 24.3 (26.3° C.) | 26.2 (25° C.) | 25.8 (24° C.) | 31.0 (25° C.) | 33.5 (25° C.) 49.2 (40° C.) | 34.7 (25° C.) 99.5 (40° C.) | 36.0 (25° C.) >100 (40° C.) |
| 2 | 14.0 (36° C.) | 18.4 (26.4° C.) | 18.0 (26.4° C.) | 19.3 (25° C.) | 23.2 (25° C.) | 25.3 (25° C.) 54.6 (40° C.) | 29.6 (25° C.) 83.9 (40° C.) | 35.6 (25° C.) >100 (40° C.) |
| 3 | 7.8 (37.8° C.) | 21.0 (30.2° C.) | 25.9 (29.1° C.) | — | 25.8 (25° C.) | 33.4 (25° C.) 37.1 (40° C.) | 34.3 (25° C.) 46.1 (40° C.) | 38.5 (25° C.) 57.8 (40° C.) |
| 4 | 24.4 (35.3° C.) | 36.2 (28.5° C.) | 37.6 (26.0° C.) | 353 (25° C.) | 45.1 (25° C.) | 45.3 (25° C.) 52.9 (40° C.) | 51.1 (25° C.) 50.1 (40° C.) | 52.3 (25° C.) 55.9 (40° C.) |
| 5 | 33.5 (38.8° C.) | 31.2 (33° C.) | 31.7 (29.4 ° C.) | 35.0 (25° C.) | 28.1 (25° C.) | 37.2 (25° C.) 50.7 (40° C.) | 39.4 (25° C.) 60.0 (40° C.) | 47.5 (25° C.) 53.4 (40° C.) |
| 6 | 20.2 (36.1° C.) | 32.9 (28.5° C.) | — | — | 44.8 (25° C.) | 45.2 (25° C.) 43.0 (40° C.) | 47.4 (25° C.) 45.5 (40° C.) | 45.8 (25° C.) 40.8 (40° C.) |
| 7 | 15.3 (36.7° C.) | 27.7 (31.8 ° C.) | — | — | 31.2 (25° C.) | 32.2 (25° C.) 35.1 (40° C.) | 32.8 (25° C.) 35.2 (40° C.) | 32.3 (25° C.) 33.8 (40° C.) |
| 8 | 11.2 (37.5° C.) | — | 26.1 (26.8° C.) | 26.9 (26.4° C.) | 29.6 (25° C.) | 25.2 (25° C.) 26.3 (40° C.) | 25.8 (25° C.) 27.6 (40° C.) | 24.3 (25° C.) 29.1 (40° C.) |
| 9 | 11.7 (36.0° C.) | 12.2 (34.1° C.) | 16.8 (28.5° C.) | 19.2 (27.2° C.) | 27.6 (25.2° C.) | 32.7 (25° C.) 32.4 (40° C.) | 30.2 (25° C.) 36.0 (40° C.) | 29.7 (25° C.) 29.3 (40° C.) |
| Control | 26.5 (35.0° C.) | 32.6 (30.0° C.) | — | — | 38.8 (25.0° C.) | 41.0 (25° C.) 36.4 (40° C.) | 42.9 (25° C.) 37.8 (25° C.) | 40.0 (25° C.) 34.5 (25° C.) |

The viscosity data in Table 2 demonstrate significant differences for the three types of gum cooperation systems with high salt level toothpaste. Formulas 1 and 2 are utilize thickener silica, Xanthan gum and carboxymethylcellulose for the thickener/binder system. It can be seen that the viscosity of these compositions is unstable, increasing significantly with time. Starting at an initial low initial viscosity of about 14-20*10$^4$ cps, the aging viscosity increases to a much greater value (greater than 100*10$^4$ cps) within three months. The resulting toothpaste is hard to squeeze out from the tubes at this viscosity. Accordingly, this type of gum system has unstable viscosity in high salt level toothpaste, which renders it unsuitable to preparation of a striped toothpaste.

Formulas 3, 4 and 5 have high levels of thickener silica and also contain carboxymethylcellulose. The viscosity data show that the viscosities of these compositions are more stable than those of Formulas 1 and 2, but nevertheless also have an increasing trend over time. Further, as discussed below, this system does not produce a good stripe quality toothpaste. While not wishing to be bound by any particular theory, it is believed that carboxymethylcellulose is a linear structure gum, and cannot form the 3-dimensional structure necessary to control the color mixing, resulting in a poor quality stripe toothpaste.

Formulas 6, 7, 8 and 9 have the carageenan-containing binder/thickener system of the present invention. It can be seen from the Table 2 that this system has a stable viscosity trend. Thus, it is believed that the presence of carrageenan in the binder/thickener system affords the maintenance and control of viscosity in high-level salt (e.g., sodium chloride) toothpaste.

Example 2—Rheology Properties Determination

Rheology and stripe filling properties are determined for toothpaste compositions having formulae 7, 8 and 9 as described in Table 1 above.

The control toothpaste is a commercial striped toothpaste which delivers a good striping quality, which does not contain sodium chloride, and includes 1.0%. Carrageenan, and 15/5/1.5 Silica (i.e. 15% abrasive siliva; 5% Sorbosil AC43, and 1.5% thickener silica).

A thixotropic test is used to predict if a formula can be striped with good stripe quality. A well-defined thixotropic loop indicates that the formula can be striped with good quality while the absence of a well-defined loop suggests that the formula cannot provide good stripe. We find the hysteresis loop test to be a useful way to measure thixotropy. We linearly increase the shear rate from zero to a maximum value and then to return at the same rate to zero. Thus a constant loop behavior is seen.

The following four samples are used in the thixotropic test:
  Sample 1: Commercial toothpaste containing 1.0% Carrageenan, and 15% abrasive thickener silica; 5% Sorbosil AC43, and 1.5% thickener silica (control sample identical to Control as described in Table 1, above);
  Sample 2: Experimental Sample containing 0.8% Carrageenan, 8% abrasive silica and 3% thickener silica; and 10% sodium chloride (identical to Formula 7 from Table 1, above);
  Sample 3: Experimental Sample containing 0.7% Carrageenan, 0.15% CMC 2000s, 8% abrasive silica; 3% thickener silica; and 10% sodium chloride (identical to Formula 8 from Table 1, above).
  Sample 4: Experimental Sample containing 0.8% Carrageenan, 0.3% CMC 2000s, 8% abrasive silica; 4% thickener silica; and 5% sodium chloride (identical to Formula 9 from Table 1, above).
Sample 1 corresponds to the control and Samples 2, 3 and 4 correspond to formulae 7, 8, and 9 respectively in above Table 1.

Figure 1:
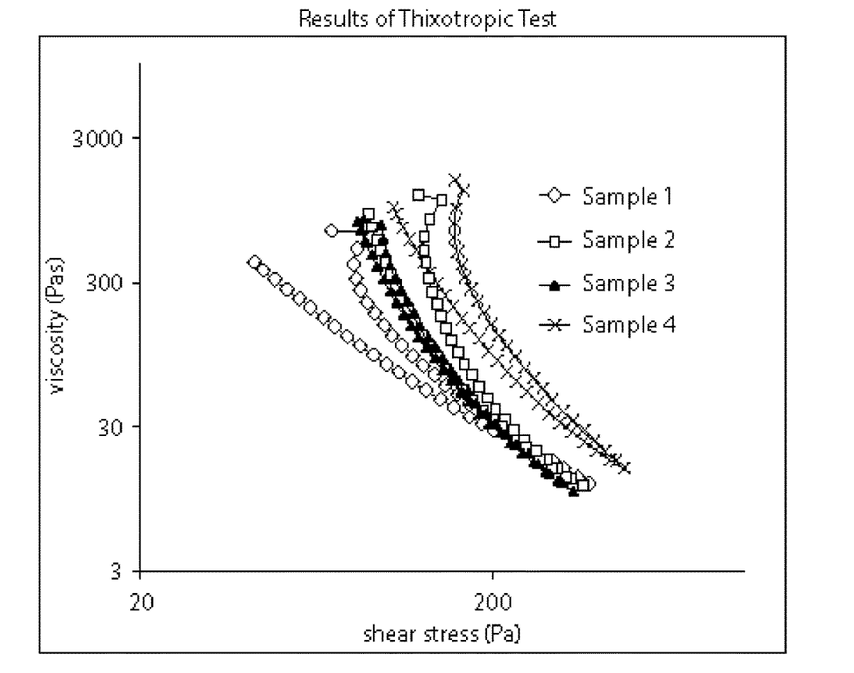
FIG. 1 shows the result of the Thixotropic Test described in Example 2.

The results of the thixotropic test are shown in FIG. 1. All three experimental samples show loop curves characteristic of materials possessing thixotropy. Accordingly, while not wishing to be bound by any particular theory it is believed that the carrageenan-based thickener provides for the formation of a three-dimensional structure, which aids in stabilizing the viscosity of the toothpaste during 3 months accelerated aging.

Example 3—Strip Quality Determination

The stripe quality index (SQI) test is used to determine if the quality of a stripe is acceptable. A commercially acceptable stripe is considered to be a stripe which has a SQI of 3 or above. The stripe quality is tested by extruding the striped toothpaste and quantitatively evaluating the stripe quality according to a stripe quality index numerical scale, where 1 represents the worst stripe quality and 5 represents the best stripe quality. Ten data points are employed for the testing of each toothpaste, each data point corresponding to a respective property of a respective extrusion (A=stripe definition, B=stripe consistency of the first short ribbons during extrusion, C=stripe definition, D=stripe consistency of the first long ribbons during extrusion, E=stripe definition, F=stripe consistency of the second short ribbons during extrusion; G=stripe definition, H=stripe consistency of the second long ribbons during extrusion; I=stripe definition, J=stripe consistency of the last short ribbons during extrusion).

Toothpaste Preparation:
(1) A proportion of humectant (sorbitol, glycerine, etc) an added into gel tank.
(2) Pigment, hot water are added into gel tank.
(3) Mixture of Gums (Carrageenan, CMC, Xanthan gum etc) with minor ingredients (NaF/MFP, Saccharin) are dispersed into gel tank and increase to definite temperature and mixing completely.
(4) The gel is transferred into the main mixer at full vacuum.
(5) The silica is allowed to be sucked into the mixer by the vacuum and mixed completely.
(6) Add the surfactant (SLS, Poloxamer 407) into mixer and mix completely.
(7) Inhale Sodium Chloride and flavour into mixer and mix completely with full vacuum.

The following four samples are used in the SQI test:
  Sample 1: Commercial toothpaste containing 1.0% Carrageenan, and 15% abrasive thickener silica; 5% Sorbosil AC43, and 1.5% thickener silica (control sample identical to Control as described in Table 1, above);
  Sample 2: Experimental Sample containing 0.8% Carrageenan, 8% abrasive silica and 3% thickener silica; and 10% sodium chloride (identical to Formula 7 from Table 1, above);
  Sample 3: Experimental Sample containing 0.7% Carrageenan, 0.15% CMC 2000s, 8% abrasive silica; 3% thickener silica; and 10% sodium chloride (identical to Formula 8 from Table 1, above).
  Sample 4: Experimental Sample containing 0.8% Carrageenan, 0.3% CMC 2000s, 8% abrasive silica; 4% thickener silica; and 5% sodium chloride (identical to Formula 9 from Table 1, above).
All three experimental samples produce a good stripe quality toothpaste, and each has an attractive translucent appearance.

While the present invention has been described with reference to embodiments, it will be understood by those skilled in the art that various modifications and variations may be made therein without departing from the scope of the present invention as defined by the appended claims.

What is claimed is:

1. A high salt toothpaste with stable viscosity comprising from 5% to 15% sodium chloride, 0.5% to 1.5% carrageenan, and 55% to 70% sorbitol, by weight of the toothpaste, wherein the toothpaste displays a viscosity of less than $50 \times 10^4$ cps during storage at 40° C. for 3 months.

2. The toothpaste of claim 1, wherein the toothpaste comprises from 8% to 12% sodium chloride by weight of the toothpaste.

3. The toothpaste of claim 1 further comprising carboxymethylcellulose in an amount of from 0.1% to 1%; or from 0.1% to 0.5% by weight of the toothpaste.

4. The toothpaste of claim 1 wherein the toothpaste comprises sorbitol in an amount of from 60% to 66%; by weight of the toothpaste.

5. The toothpaste of claim 1, further comprising one or more dispersants in an amount of from 0.5% to 2%; by weight of the toothpaste.

6. The toothpaste of claim 1, further comprising one or more thickeners in an amount of from 1% to 6%, by weight of the toothpaste.

7. The toothpaste of claim 1, further comprising one or more abrasives in an amount of from 5% to 10%, by weight of the toothpaste.

8. The toothpaste of claim 1, further comprising one or more detergents or surfactants in an amount of from 1% to 3%, and a poloxamer in an amount of from 0.5% to 2%; by weight of the toothpaste.

9. The toothpaste of claim 1, further comprising a fluoride source, in an amount of from 0.15% to 0.5%, by weight of the toothpaste.

10. The toothpaste of claim 1, comprising:
from 8% to 12% sodium chloride;
from 0.6% to 1.1% carrageenan;
optionally, from 0.1% to 0.5% CMC 2000s;
from 55% to 70% sorbitol; and
from 0.5% to 2% polyethylene glycol 600.

11. The toothpaste of claim 1, comprising:
from 5% to 10% abrasive thickener silica;
from 2% to 6% thickener silica;
from 1% to 3% sodium lauryl sulfate;
from 0.5% to 2% poloxamer 407; and
from 0.1% to 0.5% sodium fluoride.

12. The toothpaste of claim 1, comprising 60% to 65% sorbitol.

13. The toothpaste of claim 1, comprising:
from 0.1% to 0.5% sodium fluoride; and
from 1% to 3%; thickener silica.

14. The toothpaste of claim 1, further comprising one or more adjuvants selected from sweetening agents flavoring agents and coloring agents.

15. The toothpaste of claim 10, comprising a flavoring agent in an amount of from 0.5% to 3.0%.

16. The toothpaste of claim 1 comprising about 10% sodium chloride; 0.5% to 1.5% carrageenan; optionally, 0.1% to 0.5% CMC 2000s; about 63% sorbitol; about 1% polyethylene glycol; 3% to 4% thickener silica; 5% to 10% abrasive silica thickener; about 2% sodium lauryl sulfate; about 1% poloxamer 407; and 0.2% to 0.3% sodium fluoride.

17. A toothpaste comprising: sodium chloride in an amount of from 8% to 12%; a binder system comprising from 0.5% to 1.5% carrageenan, and, optionally, from 0.1% to 0.5% carboxymethylcellulose; an abrasive; one or more detergents; one or more dispersants; and a fluoride source; wherein the toothpaste is striped, translucent, and contains more sodium chloride by weight than abrasive.

18. A method for stabilizing a toothpaste having high salt concentration, comprising mixing the salt with a binder system, wherein the toothpaste comprises from 5% to 15% sodium chloride and from 55% to 70% sorbitol, and the binder system comprises from 0.5% to 1.5% carrageenan, and, optionally, from 0.1% to 0.5% carboxymethylcellulose.

19. The toothpaste of claim 5, wherein the dispersant is polyethylene glycol.

20. The toothpaste of claim 8, wherein the detergent or surfactant is sodium lauryl sulfate.

* * * * *